United States Patent

Eckhardt et al.

[11] Patent Number: 5,945,396
[45] Date of Patent: Aug. 31, 1999

[54] COMPOUNDS

[75] Inventors: Claude Eckhardt, Riedisheim; Georges Metzger, Moernach, both of France; Dieter Reinehr, Kandern; Hanspeter Sauter, Schopfheim, both of Germany; Mario Dubini, Niederdorf, Switzerland

[73] Assignee: Ciba Specialty Chemicals Corporation, Tarrytown, N.Y.

[21] Appl. No.: 08/996,895

[22] Filed: Dec. 23, 1997

[30] Foreign Application Priority Data

Dec. 24, 1996 [GB] United Kingdom .................. 9626851

[51] Int. Cl.$^6$ ...................... D06M 11/00; C07D 251/38
[52] U.S. Cl. ................ 510/521; 252/8.61; 252/8.63; 252/8.91; 510/522; 510/527; 544/194; 544/206; 544/208; 544/215; 544/216
[58] Field of Search .................. 252/8.61, 8.63, 252/8.91; 510/521, 522, 527; 544/194, 206, 208, 215, 216

[56] References Cited

U.S. PATENT DOCUMENTS

| | | | |
|---|---|---|---|
| 3,663,538 | 5/1972 | Lebkücher et al. | 260/240 B |
| 5,637,348 | 6/1997 | Thompson et al. | 427/160 |
| 5,688,758 | 11/1997 | Reinehr et al. | 510/516 |
| 5,741,905 | 4/1998 | Backer et al. | 544/194 |

FOREIGN PATENT DOCUMENTS

| | | |
|---|---|---|
| 2020666 | 1/1991 | Canada . |
| 0659877 | 6/1995 | European Pat. Off. . |
| 1129548 | 6/1967 | United Kingdom . |
| 2290803 | 10/1996 | United Kingdom . |

OTHER PUBLICATIONS

Chemical Abstract, 77, 12261p (1972).
Chemical Abstract, 88, 122671g (1978).

*Primary Examiner*—Anthony Green
*Attorney, Agent, or Firm*—Kevin T. Mansfield

[57] ABSTRACT

The present invention provides a compound having the formula:

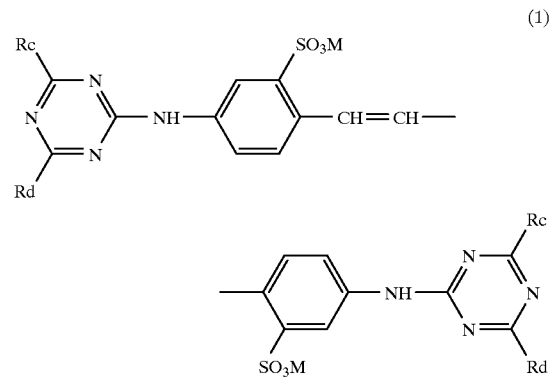

(1)

in which each $R_d$ is the same or different and each is $-NH-Z-N(R_a)(R_b)$ or $-N-[Z-N(R_a)(R_b)]_2$ in which Z is $C_2-C_{14}$alkylene or optionally substituted arylene, $R_a$ and $R_b$ are the same or different and each is $C_1-C_{12}$alkyl, or $R_a$ and $R_b$, together with the nitrogen atom to which they are each attached, form a morpholino, piperidino or piperazino ring; each $R_c$ is the same or different and is $NH_2$, $NH(C_1-C_4\text{alkyl})$, $N(C_1-C_4\text{alkyl})_2$, $N(CH_2CH_2OH)_2$, $O-C_1-C_4\text{alkyl}$,

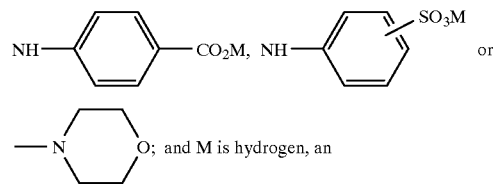

alkali metal atom, ammonium or a cation formed from an amine; or a quaternized form thereof. The present invention also relates to a composition for the treatment of textiles, in particular to a composition containing the new ultra-violet absorbing agents; and to a method for the improvement of both the sun protection factor (UPF) and the whiteness of textile fiber material, comprising treating the material with the composition according to the present invention.

24 Claims, No Drawings

COMPOUNDS

COMPOUNDS

The present invention relates to new compounds which are ultra-violet absorbing agents (UVAs). The present invention also relates to a composition for the treatment of textiles, in particular to a composition containing the new ultra-violet absorbing agents; and to a method for the improvement of both the UV protection factor (UPF) and the whiteness of textile fibre material, comprising treating the material with the composition according to the present invention.

It is known that light radiation of wavelengths 280–400 nm permits tanning of the epidermis. Also known is that rays of wavelengths 280–320 nm (termed UV-B radiation), cause erythemas and skin burning which can inhibit skin tanning.

Radiation of wavelengths 320–400 nm (termed UV-A radiation) is known to induce skin tanning but can also cause skin damage, especially to sensitive skin which is exposed to sunlight for long periods. Examples of such damage include loss of skin elasticity and the appearance of wrinkles, promotion of the onset of erythemal reaction and the inducement of phototoxic or photoallergic reactions.

Any effective protection of the skin from the damaging effects of undue exposure to sunlight clearly needs to include means for absorbing both UV-A and UV-B components of sunlight before they reach the skin surface.

Traditionally, protection of exposed human skin against potential damage by the UV components in sunlight has been effected by directly applying to the skin a preparation containing a UV absorber. In areas of the world, e.g. Australia and America, which enjoy especially sunny climates, there has been a great increase in the awareness of the potential hazards of undue exposure to sunlight, compounded by fears of the consequences of alleged damage to the ozone layer. Some of the more distressing embodiments of skin damage caused by excessive, unprotected exposure to sunlight are development of melanomas or carcinomas on the skin.

One aspect of the desire to increase the level of skin protection against sunlight has been the consideration of additional measures, over and above the direct protection of the skin. For example, consideration has been given to the provision of protection to skin covered by clothing and thus not directly exposed to sunlight.

Most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer.

There is a need, therefore, to provide protection against UV radiation for skin which lies underneath clothing, including lightweight summer clothing, which is undyed or dyed only in pale shades. Depending on the nature of the dyestuff, skin covered by clothing dyed in some dark shades may also require protection against UV radiation.

Such lightweight summer clothing normally has a density of of less than 200 g/m$^2$ and has a UPF rating between 1.5 and 20, depending on the type of fibre from which the clothing is manufactured.

The UPF rating of a sun protectant (sun cream or clothing) may be defined as the multiple of the time taken for the average person wearing the sun protectant to suffer sun burning under average exposure to sun. For example, if an average person would normally suffer sun burn after 30 minutes under standard exposure conditions, a sun protectant having an UPF rating of 5 would extend the period of protection from 30 minutes to 2 hours and 30 minutes. For people living in especially sunny climates, where mean sun burn times are minimal, e.g. only 15 minutes for an average fair-skinned person at the hottest time of the day, UPF ratings of at least 20 are desired for lightweight clothing.

It is already known, from GB-A-2 290 803, that the application, to a washed article of clothing, of a rinse cycle fabric care formulation comprising a fluorescent whitening agent, preferably a cationic, amphoteric or anionic fluorescent whitening agent, which is compatible with the fabric care ingredient, imparts an excellent whiteness and sun protection factor to the fibre material so treated.

Surprisingly, it has now been found that the application, to a washed article of clothing, of a rinse cycle fabric softener formulation comprising a specific class of new triazinylamino-stilbene ultra-violet absorbing agents according to the present invention, imparts a still further improved whiteness and UV protection factor to the fibre material so treated.

The present invention provides, as a first aspect, a compound having the formula:

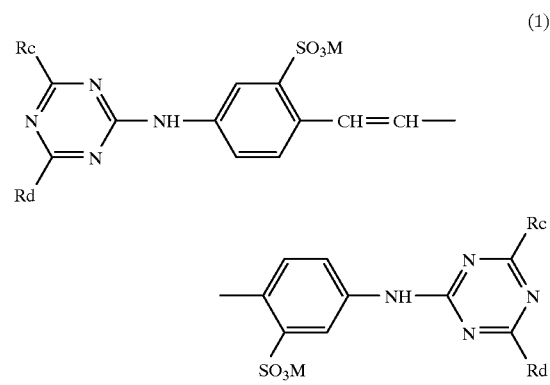

in which each $R_d$ is the same or different and each is —NH—Z—N($R_a$)($R_b$) or —N—[Z—N($R_a$)($R_b$)]$_2$ in which Z is $C_2$–$C_{14}$alkylene or optionally substituted arylene, $R_a$ and $R_b$ are the same or different and each is $C_1$–$C_{12}$alkyl, or $R_a$ and $R_b$, together with the nitrogen atom to which they are each attached, form a morpholino, piperidino or piperazino ring; $R_c$ is $NH_2$, $NH(C_1$–$C_4$alkyl), $N(C_1$–$C_4$alkyl)$_2$, $N(CH_2CH_2OH)_2$, O—$C_1$–$C_4$alkyl,

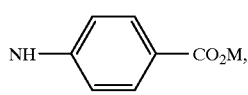

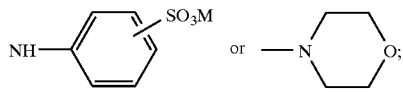

and M is hydrogen, an alkali metal atom, and M is hydrogen, an alkali metal atom, ammonium or a cation formed from an amine; or a quaternised form thereof.

$C_2$–$C_{14}$alkylene groups Z include, e.g., ethylene, 1,3-propylene, 1,4-butylene, 1,5-pentylene, 1,6-hexylene, 1,8-octylene, 1,10-decylene, 1,12-dodecylene and 1,14- tetradecylene groups. Preferred are $C_2$–$C_6$alkylene groups Z, most preferably the 1,3-propylene group. Optionally substituted arylene Z include the naphthylene and, preferably, the phenylene group. The optionally substituted arylene Z may be substituted, for example with one or more $C_1$–$C_4$alkyl groups.

$C_1$–$C_{12}$alkyl groups $R_a$ and $R_b$ may be, e.g., methyl, ethyl, n-propyl, isopropyl, n-butyl, n-pentyl, n-hexyl, n-octyl, n-decyl and n-dodecyl groups, preferably methyl or ethyl groups.

Preferably $R_a$ and $R_b$ are the same and each is a $C_1$–$C_5$alkyl group, especially methyl or ethyl.

Each $R_c$ is preferably the same and is $NH_2$.

Preferably M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium or ammonium that is di- or tri-substituted with a mixture of $C_1$–$C_4$alkyl and $C_1$–$C_4$hydroxyalkyl groups. Preferably each M is Na.

The compounds of formula (1) may in the form of the free base or in the form of a quaternary compound consisting of a cationic moiety having the formula (1) in which one of the amino groups contained therein carries a positive charge, and an anionic moiety $A^-$ in which A is an anion.

The compounds of formula (1) may be produced by reacting, under known reaction conditions, cyanuric chloride, successively, in any desired sequence, with each of 4,4'-diaminostilbene-2,2'-di-sulfonic acid, ammonia and a compound capable of introducing a group NH—Z—$NR_aR_b$ or —N—[Z—$N(R_a)(R_b)]_2$ in which Z, $R_a$ and $R_b$ have their previous significance. The necessary starting materials are known compounds which are readily available. Quaternisation of the compounds of formula (1) may be conducted by methods which are well-known. The present invention also provides, as a second aspect, a stable, concentrated rinse cycle fabric softener composition comprising 2 to 25, preferably 5 to 20% by weight of a cationic fabric softening agent and 0.3 to 10, preferably 0.3 to 3% by weight of an ultra-violet absorbing agent of formula (1A):

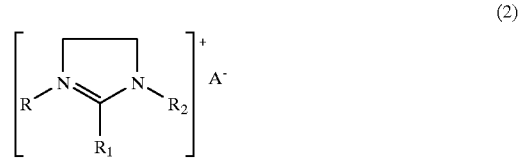

in which each $R_d$ is the same or different and each is —NH—Z—$N(R_a)(R_b)$ or —N—[Z—$N(R_a)(R_b)]_2$ in which Z is $C_2$–$C_{14}$alkylene or optionally substituted arylene, $R_a$ and $R_b$ are the same or different and each is $C_1$–$C_{12}$alkyl, or $R_a$ and $R_b$, together with the nitrogen atom to which they are each attached, form a morpholino, piperidino or piperazino ring; each $R_e$ is the same or different and is $NH_2$, $NH(C_1$–$C_4$alkyl), $N(C_1$–$C_4$alkyl)$_2$, $N(CH_2CH_2OH)_2$, O—$C_1$–$C_4$alkyl, NH—phenyl,

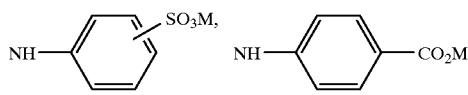

-continued

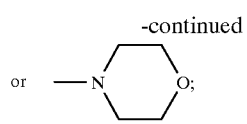

and M is hydrogen, an alkali metal atom, ammonium or a cation formed from an amine; or a quaternised form thereof; each based on the total weight of the composition, the remainder being substantially water.

Preferred examples of cationic fabric softening agents include imidazolines, quaternary ammonium compounds, ester amide amine salts, as well as mixtures thereof.

Preferred imidazoline cationic fabric softening agents are those having the formula:

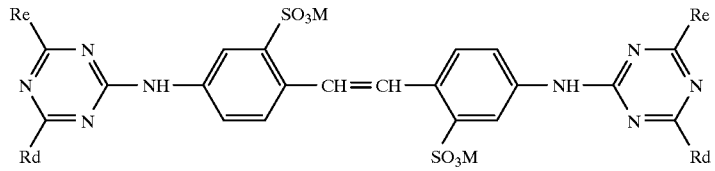

(2)

in which R is hydrogen or $C_1$–$C_4$alkyl; $R_1$ is a $C_8$–$C_{30}$aliphatic residue; $R_2$ is —$C_2H_4$—O(C=O)—$R_1$ or —$C_2H_4$—NH(C=O)—$R_1$; and A is an anion.

Preferably R is hydrogen or methyl; $R_1$ is $C_{14}$–$C_{18}$alkyl or $C_{14}$–$C_{18}$alkenyl; and $R_2$ is —$C_2H_4$—O(C=O)—$C_{14}$–$C_{18}$alkyl or —$C_{14}$–$C_{18}$alkenyl, or —$C_2H_4$—NH(C=O)—$C_{14}$–$C_{18}$alkyl or —$C_{14}$–$C_{18}$alkenyl.

Other preferred imidazoline cationic fabric softening agents are those having the formula:

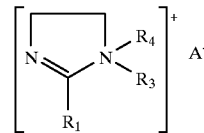

(3)

in which $R_1$ and A have their previous significance; $R_3$ and $R_4$, independently, are a $C_8$–$C_{30}$aliphatic residue, $C_1$–$C_4$alkyl, $C_1$–$C_4$halogenoalkyl, $C_1$–$C_4$hydroxyalkyl or a group —$C_2H_4$—$N(R_5)$—C(=O)—$R_6$ in which $R_5$ is hydrogen or $C_8$–$C_{30}$alkyl and $R_6$ is hydrogen or $C_1$–$C_4$alkyl.

Preferably $R_1$ is $C_{14}$–$C_{18}$alkyl or $C_{14}$–$C_{18}$alkenyl; $R_3$ is $C_{14}$–$C_{18}$alkyl, $C_{14}$–$C_{18}$alkenyl, $C_1$–$C_4$alkyl, $C_1$–$C_4$halogenoalkyl or $C_1$–$C_4$hydroxyalkyl; and $R_4$ is a group —$C_2H_4$—N($R_5$)—C(=O)—$R_6$ in which $R_5$ is hydrogen or $C_8$–$C_{30}$alkyl and $R_6$ is hydrogen or $C_1$–$C_4$alkyl.

Preferred anions A include chloride, bromide, iodide, fluoride, sulfate, methosulfate, nitrite, nitrate or phosphate anions, as well as carboxylate anions such as acetate, adipate, phthalate, benzoate, stearate or oleate anions.

Specific examples of preferred compounds of formula (2) include:

2-tallow-1-(2-stearoyloxyethyl)-imidazoline chloride, 2-tallow-1-(2-stearoyloxyethyl)-imidazoline sulfate, 2-tallow-1-(2-stearoyloxyethyl)-imidazoline methosulfate, 2-tallow-1-methyl-3-(2-stearoylamidoethyl)-imidazoline chloride, 2-tallow-1-methyl-3-(2-stearoylamidoethyl)-imidazoline sulfate and 2-tallow-1-methyl-3-(2-stearoylamidoethyl)-imidazoline methosulfate.

Specific examples of preferred compounds of formula (3) include:

2-heptadecyl-1-methyl-1-oleylamidoethyl-imidazolinium-metho-sulfate, 2-heptadecyl-1-methyl-1-(2-stearoylamido)ethyl-imidazolinium-sulfate, 2-heptadecyl-1-methyl-1-(2-stearoylamido)ethyl-imidazolinium-chloride, 2-coco-1-(2-hydroxyethyl)-1-benzyl-imidazolinium-chloride, 2-coco-1-(2-hydroxyethyl)-1-(4-chlorobutyl)-imidazolinium-chloride, 2-coco-1-(2-hydroxyethyl)-1-octadecenyl-imidazolinium-chloride, 2-tallow-1-(2-hydroxyethyl)-1-benzyl-imidazolinium-chloride, 2-tallow-1-(2-hydroxyethyl)-1-(4-chlorobutyl)-imidazolinium-chloride, 2-heptadecenyl-1-(2-hydroxyethyl)-1-(4-chlorobutyl)-imidazolinium-chloride, 2-heptadecenyl-1-(2-hydroxyethyl)-1-benzyl-imidazolinium-chloride and 2-heptadecenyl-1-(2-hydroxyethyl)-1-octadecyl-imidazolinium-chloride.

One class of preferred quaternary ammonium compounds is that having the formula:

(4)

in which $R_7$ is a $C_8$–$C_{30}$aliphatic residue, $R_8$, $R_9$, $R_{10}$, $R_{11}$ and $R_{12}$, independently, are hydrogen, $C_1$–$C_4$alkyl or $C_1$–$C_4$hydroxyalkyl, A has its previous significance, m is an integer from 1 to 5 and n is an integer from 2 to 6.

Preferred compounds of formula (4) are those in which $R_7$ is $C_{12}$–$C_{18}$alkyl and $R_8$, $R_9$, $R_{10}$, $R_{11}$ and $R_{12}$, independently, are $C_1$–$C_4$alkyl, especially methyl.

Specific examples of preferred compounds of formula (4) are:

N-(tallow)-N,N,N',N'-tetramethyl-1,3-propanediammoniumdimethosulfate,

N-(tallow)-N,N',N'-trimethyl-1,3-propanediammoniumdimethosulfate,

N-(tallow)-N,N,N',N'-pentamethyl-1,3-propanediammoniumdimethosulfate,

N-oleyl-N, N,N',N'-pentamethyl-1,3-propanediammoniumdimethosulfate,

N-stearyl-N,N,N',N'-pentamethyl-1,3-propanediammoniumdimethosulfate and

N-stearyloxypropyl-N,N',N'-tris(3-hydroxypropyl)-1,3-propanediammoniumdiacetate.

A further class of preferred quaternary ammonium compounds is that having the formula:

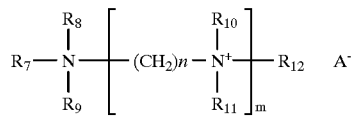

(5)

in which A has its previous significance and the groups $R_{13}$ may be the same or different and each is a $C_1$–$C_{30}$aliphatic residue, $C_1$–$C_4$hydroxyalkyl, $C_2H_4OC(=O)$—$R_1$, $C_2H_4NHC(=O)$—$R_1$ or $CH_2CH[OC(=O)$—$R_1][CH_2OC(=O)$—$R_1]$, provided that at least one group $R_{13}$, and preferably two groups $R_{13}$ are $C_{14}$–$C_{30}$alkyl, $C_2H_4OC(=O)$—$C_{14}$–$C_{30}$alkyl, $C_2H_4NHC(=O)$—$C_{14}$–$C_{30}$alkyl or $CH_2CH[OC(=O)$—$C_{14}$–$C_{30}$alkyl][$CH_2OC(=O)$—$C_{14}$–$C_{30}$alkyl]. Preferably, the remaining groups $R_{13}$ are $C_1$–$C_4$alkyl, especially methyl or ethyl, or $C_1$–$C_4$hydroxyalkyl, especially hydroxymethyl or hydroxyethyl.

Specific examples of preferred compounds of formula (5) are:

distearyldimethylammonium chloride, dilauryidimethylammonium chloride, dihexadecyldimethylammonium chloride, distearyldimethylammonium bromide, distearyidimethylammonium methosulfate, distearyldi-(isopropyl)-ammonium chloride and distearoyl(hydroxyethyl)methylammonium methosulfate.

Preferred ester amide amine cationic fabric softening agents are those having the formula:

(6)

in which $R_{13}$ has its previous significance and $A_1$ is an inorganic or organic acid from which an anion A is derived, wherein A has its previous significance, provided that at least one group $R_{13}$, and preferably two groups $R_{13}$ are $C_{14}$–$C_{30}$alkyl, $(CH_2)_nOC(=O)$—$C_{14}$–$C_{30}$alkyl, $(CH_2)_nNHC(=O)$—$C_{14}$–$C_{30}$alkyl or $CH_2CH[OC(=O)$—$C_{14}$–$C_{30}$alkyl][$CH_2OC(=O)$—$C_{14}$–$C_{30}$alkyl]$, in which n has its previous significance. Preferably, the remaining groups $R_{13}$ are $C_1$–$C_4$alkyl, especially methyl or ethyl, or $C_1$–$C_4$hydroxyalkyl, especially hydroxymethyl or hydroxyethyl.

A preferred compound of formula (5) is:
3-stearoylamidopropyl-2-stearoyloxymethyl-methylamine hydrochloride.

In addition to the cationic fabric softening agent and the ultra-violet absorbing agent, the rinse cycle fabric softener composition according to the present invention may also contain a minor proportion of one or more adjuvants. Examples of adjuvants include emulsifiers, perfumes, colouring dyes, opacifiers, further UV absorbers, fluorescent whitening agents, bactericides, nonionic surfactants, anti-gelling agents such as nitrites or nitrates of alkali metals, especially sodium nitrate, and corrosion inhibitors such as sodium silicate.

The amount of each of these optional adjuvants should not exceed 2% by weight of the composition.

The present invention also provides, as a third aspect, a method for the improvement of the UPF of a textile article, comprising applying, to a previously washed article, a fabric rinse composition according to the second aspect of the present invention.

The textile article treated according to the method of the present invention may be composed of any of a wide range of types of fibre such as wool, polyamide, cotton, polyester, polyacrylic, silk or any mixture thereof.

The method and composition of the present invention, in addition to providing an improved whiteness and UPF to the washed textile article, and thereby enhanced protection to the skin, may also increase the useful life of a textile article treated according to the present invention, e.g. by improving the tear strength and lightfastness of textile articles so treated.

The following Examples further illustrate the present invention.

EXAMPLE 1

3 g of the compound having the formula:

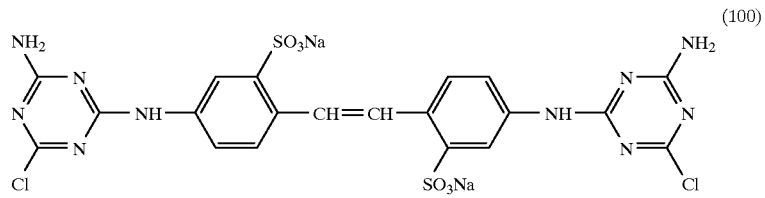

as the undecahydrate, are quickly heated with 8 g of 1-methylpiperazine to reflux using an oil bath having a bath temperature of 150° C. The reaction mixture is then cooled, whereupon a yellow oil is obtained. The oil is introduced into 200 mls of acetone and a yellowish-beige precipitate is formed. The precipitate is filtered off with suction and dried. The dried filter-cake is dissolved in 40 mls of water and, after a short time, there is precipitated, as a zwitterion, the amphoteric compound having the formula:

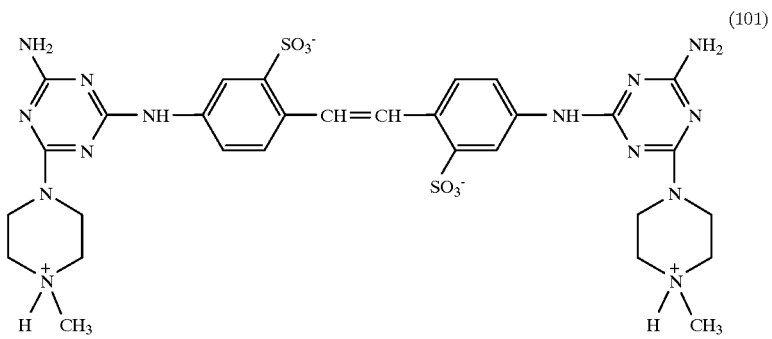

The reaction mixture is filtered off with suction and, after drying, there are obtained 2.5 g of the compound of formula (101) as light beige crystals, representing a yield of 82% of theory.

Elemental analysis of the compound having the formula (101) and having the empirical formula $C_{30}H_{38}N_{14}S_2.6.1$ $H_2O$ gives: Req. % C 40.9; H 5.95; N 22.25; S 7.27; $H_2O$ 14.30. Found % C 40.8; H 5.9; N 22.1; S 7.3; $H_2O$ 14.30.

By the addition of the stoichiometric amount of NaOH in methanol, the compound of formula (101) is converted into the corresponding di-sodium salt.

EXAMPLE 2

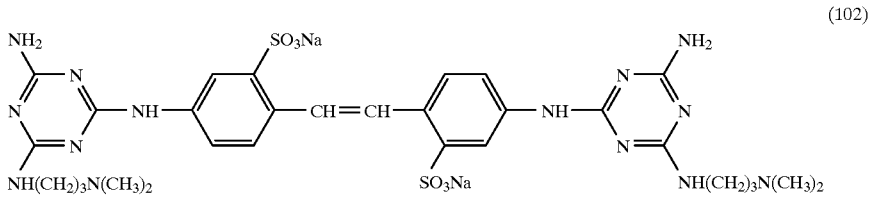
(102)

20 g of the compound of formula (100) as described in Example 1 are introduced into 80 mls of 3-dimethylamino-1-propylamine over a period of 10 minutes, whereupon an exothermic reaction set in. The reaction mixture is then stirred for 1 hour in an oil bath which is held at 90° C. The oily reaction mixture so obtained is stirred into 500 mls of acetone. Colourless crystals are precipitated which are filtered off with suction and washed with acetone to give 25.2 g of the compound of formula (102) as the 3-dimethylamino-1-propylamine salt. This salt is introduced into 200 mls of hot water and boiled for 1 hour, whereupon the corresponding amphoteric compound crystallises out as the zwitterion.

The reaction mixture is filtered off with suction and, after drying, there are obtained 15.2 g of beige crystals, representing a yield of 78.5% of theory.

Elemental analysis of the compound having the formula (102) and having the empirical formula $C_{30}H_{42}N_{14}O_6S_2 \cdot 4 H_2O$ gives: Req. % C 43.3; H 6.07; N 23.58; S 7.71; $H_2O$ 8.75. Found % C 43.10; H 5.92; N 23.55; S 7.69; $H_2O$ 8.76.

By the addition of the stoichiometric amount of sodium methylate, the corresponding di-sodium salt compound of formula (102) in methanol is obtained.

Using the procedure described in Example 2, but replacing 3-dimethylamino-1-propylamine with 3-diethylamino-1-propylamine, the compound of formula (103) is obtained in similar yield.

Elemental analysis of the di-sodium salt compound having the formula (103) and having the empirical formula $C_{34}H_{48}N_{14}O_6S_2Na_2$ 7.5 $H_2O$ gives: Req. % C 41.08; H 6.38; N 19.72; S 6.45; $H_2O$ 8.75. Found % C 41.24; H 6.20; N 19.78; S 6.24; $H_2O$ 8.76.

EXAMPLE 3

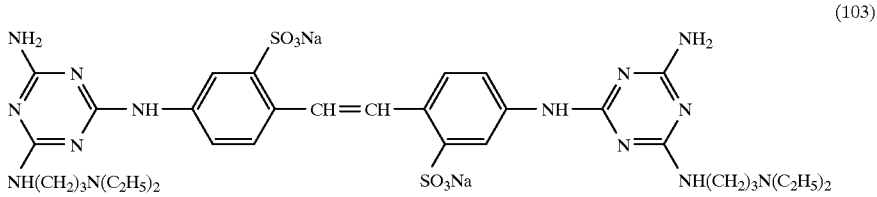
(103)

EXAMPLE 4

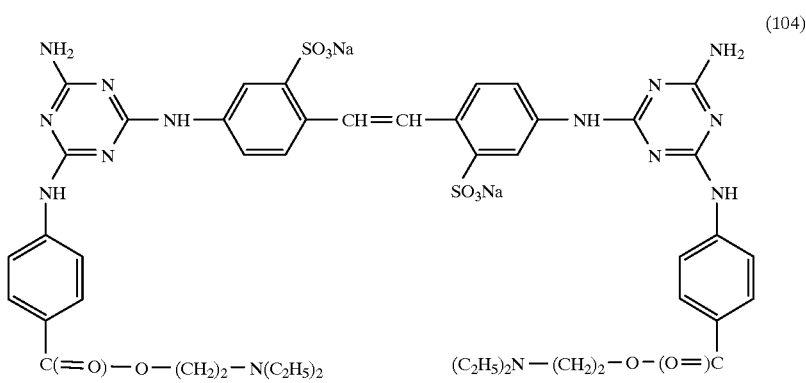

2 g of the compound of formula (100) as described in Example 1 are added to 15 g of procaine hydrochloride and the mixture is held at 170° C. for 1 hour. A honey-like mass is obtained which is stirred into 250 ml of water. After 10 minutes, the aqueous mixture is filtered off with suction and washed. After drying, there are obtained 2.5 g (90% of theory) of the compound of formula (104).

Elemental analysis of the di-sodium salt compound having the formula (104) and having the empirical formula $C_{46}H_{52}N_{14}O_{10}S_2Na_2$ 6 $H_2O$ gives: Req. % C 47.17; H 5.84; N 16.74; S 5.47; $H_2O$ 9.22. Found % C 47.00; H 5.60; N 16.60; S 5.50; $H_2O$ 9.20.

EXAMPLE 5

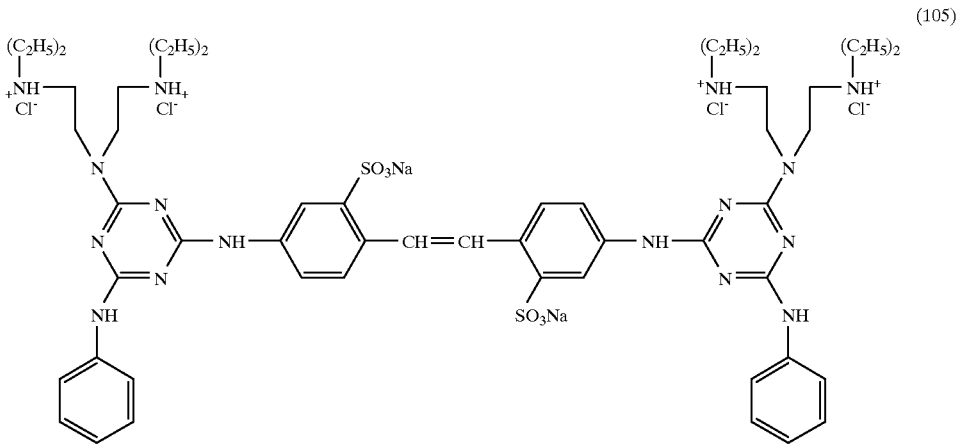

6.12 g of the compound having the formula:

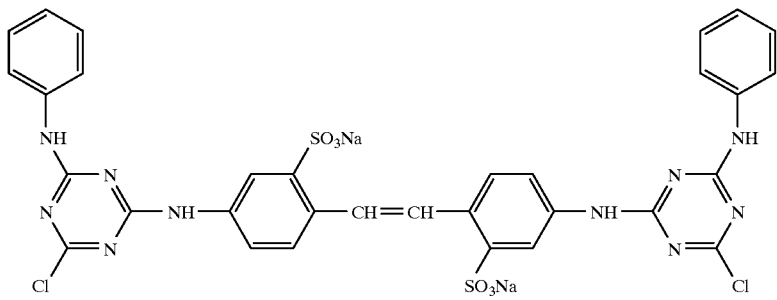

(105A)

are dissolved in 100 ml of water and 30 ml of acetone, treated with 3.37 g of N,N,N',N'-tetraethyldiethylenetriamine and 7.44 ml of 1 molar soda solution and the mixture is boiled under reflux for 30 minutes. A finely flocculated precipitate is obtained which is filtered off with suction, stirred with 5 ml of concentrated HCl in 100 ml of acetone to isolate the free acid and washed with acetone. After drying in air, there are obtained 7.2 g (65% of theory) of the compound of formula (105).

Elemental analysis of the di-sodium salt compound having the formula (105) and having the empirical formula $C_{56}H_{82}N_{16}O_6S_2Cl_4Na_2$ 10 $H_2O$ gives: Req. % C 44.56; H 6.94; N 14.84; S 4.25; Cl 9.39. Found % C 44.55; H 6.81; N 14.85; S 4.29; Cl 9.82.

are dissolved in 100 ml of water and 30 ml of acetone, treated with 3.7 g of N,N,N',N'-tetraethyldiethylenetriamine and 16 ml of 1 molar soda solution and the mixture is boiled under reflux at 75° C. for 30 minutes. A finely flocculated precipitate is obtained. The reaction mixture is stirred with 5 ml of concentrated HCl in 1000 ml of acetone to isolate the free acid, filtered off with suction and washed with acetone. The filter residue is adjusted to pH 9.5 in 100 ml of water and evaporated to dryness. There are obtained 14.6 g of the compound having the formula:

EXAMPLE 6

5.25 g of the compound having the formula:

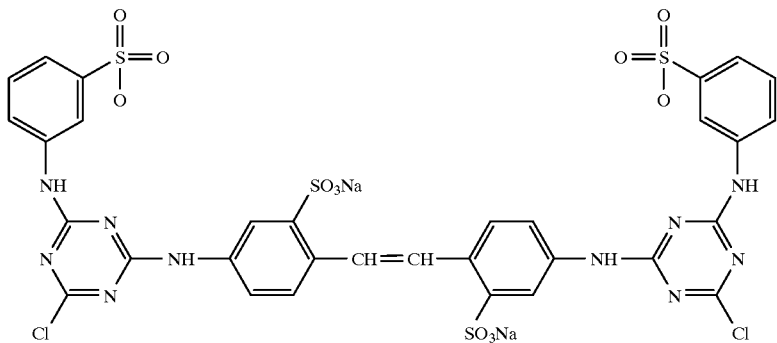

(106A)

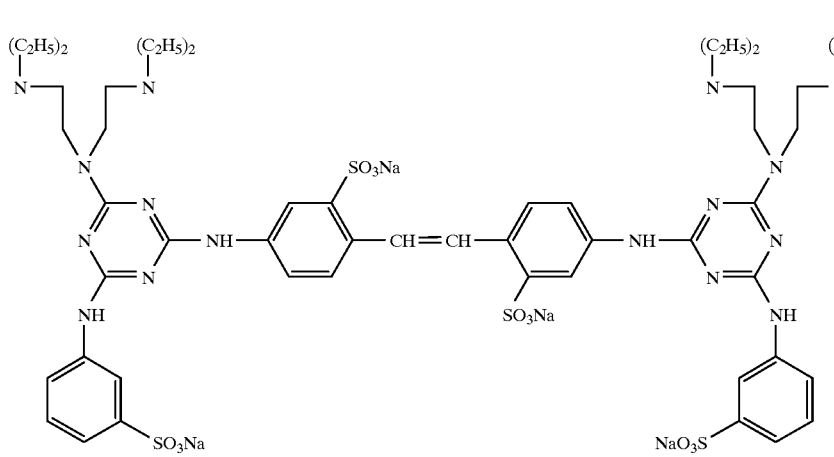

(106)

Elemental analysis of the tetra-sodium salt compound having the formula (106) and having the empirical formula $C_{56}H_{76}N_{16}O_{12}Na_4S_4$ 12 NaCl 14 $H_2O$ gives: Req. % C 29.32; H 4.56; N 9.76; S 5.59; Cl 18.54. Found % C 29.10; H 4.50; N 9.70; S 5.80; Cl 18.20.

EXAMPLE 7

19.9 g of the compound having the formula:

evaporation to dryness, the residual red oil is adjusted to pH 5 in 500 ml of water using 10.5 g of concentrated HCl. The free acid is filtered off with suction and washed with 500 ml of water. The filtercake is adjusted to pH 8 in 500 ml of water using 20.2 ml of 2N aqueous caustic soda, filtered, treated with active charcoal and evaporated to dryness. There remains 18.5 g (87% theory) of the compound having the formula:

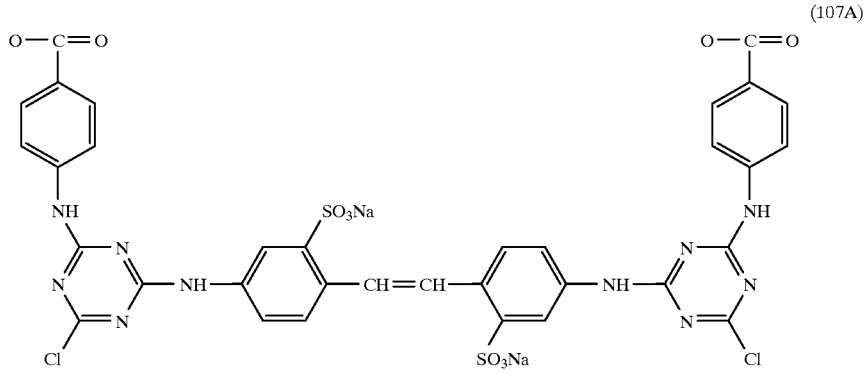

(107A)

in 330 ml of methylcellosolve are stirred with 18.2 g of 2-dimethylaminoethylamine for 1 hour at 100° C. After

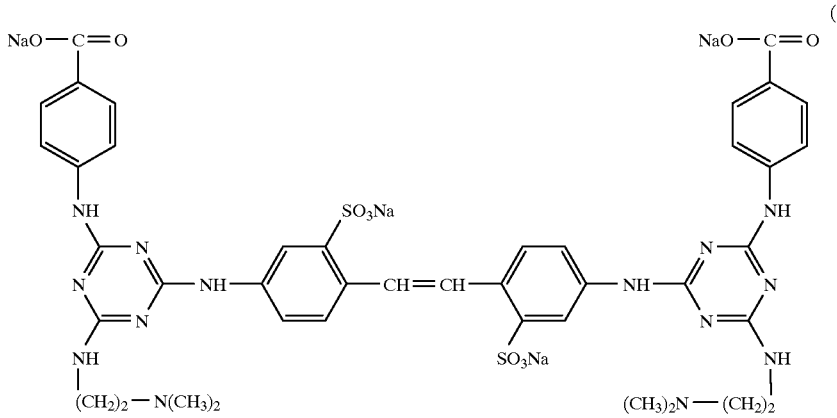

(107)

Elemental analysis of the tetra-sodium salt compound having the formula (107) and having the empirical formula $C_{42}H_{44}N_{14}Na_4O_{10}S_2$ 8.2 $H_2O$ gives: Req. % C 43.38; H 5.19; N 16.86; S 5.50; $H_2O$ 12.69; Na 3.95. Found % C 43.20; H 5.20; N 16.70; S 5.40; $H_2O$ 12.30; Na 4.30.

EXAMPLE 8

The following rinse cycle softener base composition is made up:

- 5.0 g. distearyldimethylammonium chloride (7.0 g of commercial form containing 72% active ingedient);
- 0.5 g. fatty alcohol ethoxylate ($C_{12}$–$C_{13}$-alkyl chain with 6.5 ethylene oxide units); and
- 92.5 g. deionised water.

To this is added 0.3 g., 0.9 g. or 2.7 g., respectively, of the ultra-violet absorbing agent of formula (102).

EXAMPLE 9

The following rinse cycle softener base composition is made up:

- 5.0 g. distearyldimethylammonium chloride (7.0 g of commercial form containing 72% active ingedient);
- 0.5 g. fatty alcohol ethoxylate ($C_{12}$–$C_{13}$-alkyl chain with 6.5 ethylene oxide units); and
- 92.5 g. deionised water. 7.0 g.

To this is added 0.3 g., 0.9 g. or 2.7 g., respectively, of the ultra-violet absorbing agent of formula (103).

EXAMPLES 10 and 11

5 g. of cotton fabric are first washed with 4 g/l of ECE standard detergent using a liquor ratio of 1:20 at 60° C. The washed goods are then rinsed and are subjected, while still wet, to a rinse softener treatment. The amount of the rinse cycle softener base composition of Example 8 or 9 used is 5 g/l. The liquor ratio is 1:40 using tap water and the treatment is effected at 25° C. for 10 minutes. The softener-treated goods are then spin-dried at 60° C.

The whiteness and UPF values of the dried softener-treated goods are measured.

The dried softener-treated goods are then re-washed using the same detergent and washing conditions that are used for the initial wash except that, after the rinse, the re-washed goods are spin-dried at 60° C. without being subjected to a rinse softener treatment. The whiteness and UPF values of the re-washed, dried goods are measured.

The whiteness values of the respective dried goods are measured with a DCI/SF 500 spectrophotometer according to the Ganz method. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972).

The UV Protection Factor (UPF) is determined by measurement of the UV light transmitted through the swatch, using a double grating spectrophotometer fitted with an Ulbricht bowl. Calculation of UPF is conducted as described by B. L. Diffey and J. Robson in J. Soc. Cosm. Chem. 40 (1989), pp. 130–131.

The results are shown in the following Table.

TABLE

| Example | Rinse composition | Conc. UVA | without re-wash GW | without re-wash UPF | with re-wash GW | with re-wash UPF |
|---|---|---|---|---|---|---|
| — | control | 0 | 62 | 3 | 57 | 3 |
| 10 | Ex. 8 | 0.3% | 202 | 8 | 209 | |
| | | 0.9% | 225 | 14 | 230 | |
| | | 2.7% | 227 | 21 | 233 | 16 |
| 11 | Ex. 9 | 0.3% | 176 | 5.5 | 168 | |
| | | 0.9% | 204 | 9.5 | 195 | |
| | | 2.7% | 211 | 17 | 208 | 10 |

The concentration of UVA denotes the concentration of active UVA compound based on the total weight of the rinse formulation.

The results in the Table clearly demonstrate the improvement in the Ganz Whiteness and UPF values of a cotton substrate treated with a rinse composition according to the present invention, both before and after a subsequent re-wash.

We claim:

1. A compound having the formula:

[Structure (1): A stilbene compound with two triazine groups. One end: Rc and Rd substituted triazine connected via NH to a phenyl bearing SO₃M, connected via CH=CH to another phenyl bearing SO₃M, connected via NH to another triazine with Rc and Rd substituents.]

in which each $R_d$ is the same or different and each is —NH—Z—N($R_a$)($R_b$) or —N—[Z—N($R_a$)($R_b$)]$_2$ in which Z is $C_2$–$C_{14}$alkylene or optionally substituted arylene, $R_a$ and $R_b$ are the same or different and each is $C_1$–$C_{12}$alkyl, or $R_a$ and $R_b$, together with the nitrogen atom to which they are each attached, form a morpholino, piperidino or piperazino ring; each $R_c$ is the same or different and is $NH_2$, $NH(C_1$–$C_4$alkyl), $N(C_1$–$C_4$alkyl)$_2$, $N(CH_2CH_2OH)_2$, O—$C_1$–$C_4$alkyl,

[Structures: NH—phenyl—CO₂M, or —N(morpholino)—O; and M is]

alkali metal atom, ammonium or a cation formed from an amine; or a quaternised form thereof.

2. A compound according to claim 1 in which Z is ethylene, 1,3-propylene, 1,4-butylene, 1,5-pentylene or 1,6-hexylene group.

3. A compound according to claim 2 in which Z is 1,3-propylene.

4. A compound according to claim 1 in which $R_a$ and $R_b$ are methyl, ethyl, n-propyl, isopropyl, n-butyl or n-pentyl.

5. A compound according to claim 4 in which $R_a$ and $R_b$ are the same and each is methyl or ethyl.

6. A compound according to claim 1 in which $R_c$ is $NH_2$.

7. A compound according to claim 1 in which M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium or ammonium that is di- or tri-substituted with a mixture of $C_1$–$C_4$alkyl and $C_1$–$C_4$hydroxyalkyl groups.

8. A compound according to claim 7 in which each M is Na.

9. A stable, concentrated rinse cycle fabric softener composition comprising 5 to 25% by weight of a cationic fabric softening agent and 0.3 to 10% by weight of an ultra-violet absorbing agent of formula:

[Structure (1A): stilbene bis-triazine with Re, Rd substituents and SO₃M groups]

in which each $R_d$ is the same or different and each is —NH—Z—N($R_a$)($R_b$) or —N—[Z—N($R_a$)($R_b$)]$_2$ in which Z is $C_2$–$C_{14}$alkylene or optionally substituted arylene, $R_a$ and $R_b$ are the same or different and each is $C_1$–$C_{12}$alkyl, or $R_a$ and $R_b$, together with the nitrogen atom to which they are each attached, form a morpholino, piperidino or piperazino ring; each $R_e$ is the same or different and is $NH_2$, $NH(C_1$–$C_4$alkyl), $N(C_1$–$C_4$alkyl)$_2$, $N(CH_2CH_2OH)_2$, O—$C_1$–$C_4$alkyl,

[Structures: NH-phenyl, NH—phenyl—SO₃M; NH—phenyl—CO₂M or —N(morpholino)—O; and M is]

hydrogen, an alkali metal atom, ammonium or a cation formed from an amine; or a quaternised form thereof; each based on the total weight of the composition, the remainder being substantially water.

10. A composition according to claim 9 comprising 10 to 20% by weight of a cationic fabric softening agent and 0.3 to 3% by weight of an ultra-violet absorbing agent of formula (1A), each based on the total weight of the composition, the remainder being substantially water.

11. A composition according to claim 9 in which the cationic fabric softening agent is an imidazoline, a quaternary ammonium compound, an ester amide amine salt or a mixture thereof.

12. A composition according to claim 11 in which the imidazoline cationic fabric softening agent has the formula:

[Structure (2): imidazolinium cation with R, R₁, R₂ substituents and A⁻ anion]

in which R is hydrogen or $C_1$–$C_4$alkyl; $R_1$ is a $C_8$–$C_{30}$aliphatic residue; $R_2$ is —$C_2H_4$—O(C=O)—$R_1$ or —$C_2H_4$—NH(C=O)—$R_1$; and A is an anion.

13. A composition according to claim 11 in which the quaternary ammonium compound has the formula:

[Structure (4): R₇—N(R₈)(R₉)—[(CH₂)n—N⁺(R₁₀)(R₁₁)—R₁₂]ₘ  A⁻]

in which $R_7$ is a $C_8$–$C_{30}$aliphatic residue, $R_8$, $R_9$, $R_{10}$, $R_{11}$ and $R_{12}$, independently, are hydrogen, $C_1$–$C_4$alkyl or $C_1$–$C_4$hydroxyalkyl, A is as defined in claim 12, m is an integer from 1 to 5 and n is an integer from 2 to 6.

14. A composition according to claim 11 in which the quaternary ammonium compound has the formula:

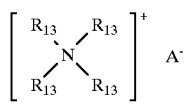

(5)

in which A is an anion and the groups $R_{13}$ may be the same or different and each is a $C_1$–$C_{30}$aliphatic residue, $C_1$–$C_4$hydroxyalkyl, $C_2H_4OC(=O)$—$R_1$, $C_2H_4NHC(=O)$—$R_1$ or $CH_2CH[OC(=O)$—$R_1][CH_2OC(=O)$—$R_1]$, provided that at least one group $R_{13}$ is $C_{14}$–$C_{30}$alkyl, $C_2H_4OC(=O)$—$C_{14}$–$C_{30}$alkyl, $C_2H_4NHC(=O)$—$C_{14}$–$C_{30}$alkyl or $CH_2CH[OC(=O)$—$C_{14}$–$C_{30}$alkyl][$CH_2OC(=O)$—$C_{14}$–$C_{30}$alkyl].

15. A composition according to claim 12 in which A is a chloride, bromide, iodide, fluoride, sulfate, methosulfate, nitrite, nitrate or phosphate anion, or a carboxylate anion.

16. A composition according to claim 9 which also contains up to 2% by weight of the composition of at least one adjuvant selected from the group consisting of an emulsifier, perfume, colouring dye, opacifier, a UV absorber which is not a compound of formula (1A), a fluorescent whitening agent, a bactericide, a nonionic surfactant, an anti-gelling agent and a corrosion inhibitor.

17. A composition according to claim 16 in which the anti-gelling agent is a nitrite or nitrate of an alkali metal and the corrosion inhibitor is sodium silicate.

18. A composition according to claim 11 in which the imidazoline cationic fabric softening agent has the formula:

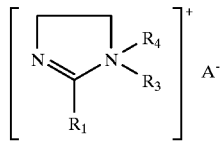

(3)

in which $R_1$ is a $C_8$–$C_{30}$aliphatic residue;

$R_3$ and $R_4$, independently, are a $C_8$–$C_{30}$aliphatic residue, $C_1$–$C_4$alkyl, $C_1$–$C_4$halogenoalkyl, $C_1$–$C_4$hydroxyalkyl or a group —$C_2H_4$—$N(R_5)$—$C(=O)$—$R_6$ in which $R_5$ is hydrogen or $C_8$–$C_{30}$alkyl $R_6$ is hydrogen or $C_1$–$C_4$alkyl and A is an anion.

19. A composition according to claim 11 in which the imidazoline cationic fabric softening agent has the formula:

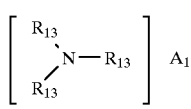

(6)

in which the groups $R_{13}$ may be the same or different and each is a $C_1$–$C_{30}$aliphatic residue, $C_1$–$C_4$hydroxyalkyl, $C_2H_4OC(=O)$—$R_1$, $C_2H_4NHC(=O)$—$R_1$ or $CH_2CH(OC(=O)$—$R_1)(CH_2OC(=O)$—$R_1)$, and $A_1$ is an inorganic or organic acid from which an anion A is derived, wherein A is an anion; provided that at least one group $R_{13}$ is $C_{14}$–$C_{30}$alkyl, $(CH_2)_nOC(=O)$—$C_{14}$–$C_{30}$alkyl, $(CH_2)_nNHC(=O)$—$C_{14}$–$C_{30}$alkyl or $CH_2CH(OC(=O)$—$C_{14}$–$C_{30}$alkyl)($CH_2OC(=O)$—$C_{14}$–$C_{30}$alkyl), in which n is an integer from 2 to 6.

20. A composition according to claim 19 in which the compound of formula (6) is: 3-stearoylamidipropyl-2-stearoyloxymethyl-methylamine hydrochloride.

21. A method for the improvement of the Ultra-Violet Protection Factor of a textile article, comprising applying, to a previously washed article, a rinse cycle fabric softener composition comprising 5 to 25% by weight of a cationic fabric softening agent and 0.3 to 10% by weight of a compound of formula (1) as defined in claim 1, each based on the total weight of the composition, the remainder being substantially water.

22. A method according to claim 21 in which the rinse cycle fabric softener composition comprises 10 to 20% by weight of a cationic fabric softening agent which is an imidazoline, a quaternary ammonium compound, an ester amide amine salt or a mixture thereof, and 0.3 to 3% by weight of the compound of formula (1), each based on the total weight of the composition, the remainder being substantially water.

23. A method according to claim 21, in which the textile article treated is composed of wool, polyamide, cotton, polyester, polyacrylic, silk or any mixture thereof.

24. A method according to claim 21 whereby tear strength and/or lightfastness of the treated textile article is improved.

* * * * *